United States Patent [19]

Schnur

[11] 4,305,877
[45] Dec. 15, 1981

[54] NOVEL SPIRO-OXAZOLIDINDIONES

[75] Inventor: Rodney C. Schnur, Noank, Conn.

[73] Assignee: Pfizer Inc., New York, N.Y.

[21] Appl. No.: 205,559

[22] Filed: Nov. 10, 1980

Related U.S. Application Data

[62] Division of Ser. No. 89,686, Oct. 30, 1979, Pat. No. 4,267,342, which is a division of Ser. No. 935,199, Aug. 21, 1978, Pat. No. 4,200,642.

[51] Int. Cl.³ .................. C07D 311/22; C07D 313/08; C07D 335/06; C07D 337/08
[52] U.S. Cl. .............................. 260/345.2; 260/333; 549/9; 549/23
[58] Field of Search .................. 260/345.2, 345.5, 333; 549/9, 23

[56] References Cited

U.S. PATENT DOCUMENTS 3,692,796  9/1972  Freedman .................. 260/345.2
3,888,873  6/1975  Freedman .................. 549/23

*Primary Examiner*—Nicky Chan
*Attorney, Agent, or Firm*—Francis X. Murphy; Charles J. Knuth; Peter C. Richardson

[57] ABSTRACT

Novel spiro-oxazolidindiones useful as aldose reductase inhibitors and as therapeutic agents for the treatment of chronic diabetic complications are disclosed. Pharmaceutical compositions containing the novel compounds and a method of treating chronic diabetic complications are also disclosed.

4 Claims, No Drawings

NOVEL SPIRO-OXAZOLIDINDIONES

This application is a division of application Ser. No. 89,686 filed Oct. 30, 1979 now U.S. Pat. No. 4,267,342; which is a division of application Ser. No. 935,199, filed Aug. 21, 1978, now U.S. Pat. No. 4,200,642.

BACKGROUND OF THE INVENTION

This invention relates to novel spiro-oxazolidindiones useful in the treatment of certain chronic complications arising from diabetes mellitus, such as diabetic cataracts and neuropathy, to intermediates for the preparation thereof, to pharmaceutical compositions containing such compounds and to a method of using these compounds.

In the past various attempts have been made to obtain novel, more effective oral anti-diabetic agents. Generally these efforts have involved synthesis of new organic compounds, particularly sulfonyl ureas, and determination of their ability to substantially lower blood sugar levels when administered orally. However, little is known about the effect of organic compounds in preventing or alleviating chronic complications of diabetes, such as diabetic cataracts, neuropathy and retinopathy. U.S. Pat. No. 3,821,383 discloses aldose reductase inhibitors like 1,3-dioxo-1H-benz[d,e]-isoquinoline-2(3H)-acetic acid and derivatives thereof to be useful for the treatment of these conditions. Such aldose reductase inhibitors function by inhibiting the activity of the enzyme aldose reductase, which is primarily responsible for regulating the reduction of aldoses such as glucose and galactose, to the corresponding polyols, such as sorbitol and galactitol, in humans and other animals. In this way unwanted accumulations of galactitol in the lens of galactosemic subjects and of sorbitol in the lens, of peripheral nervous cord and kidneys of various diabetic subjects are prevented or reduced. Accordingly, such compounds are of therapeutic value as aldose reductase inhibitors for controlling certain chronic diabetic complications, including those of an ocular nature, since it is known in the art that the presence of polyols in the lens of the eye leads to cataract formation, with a concomitant loss of lens clarity.

SUMMARY OF THE INVENTION

The present invention relates to novel aldose reductase inhibitors useful as therapeutic agents for preventing or alleviating chronic diabetic complications. Specifically, the compounds of the present invention are novel spiro-oxazolidindiones of the formula

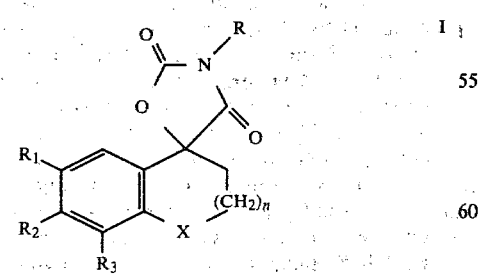

and the pharmaceutically acceptable salts thereof, wherein X is selected from the group consisting of oxygen and sulfur; n is 1 or 2; R is selected from the group consisting of hydrogen, alkyl of 1 to 4 carbon atoms, benzyl and monosubstituted benzyl, wherein said substituent is selected from the group consisting of chloro, bromo, fluoro, hydroxy, alkyl of 1 to 3 carbon atoms and alkoxy of 1 to 3 carbon atoms; and $R_1$, $R_2$ and $R_3$ are each selected from the group consisting of hydrogen, chloro, bromo, fluoro, alkyl of 1 to 3 carbon atoms, phenyl and monosubstituted phenyl, wherein said substituent is selected from the group consisting of chloro, bromo, fluoro, hydroxy, alkyl of 1 to 3 carbon atoms and alkoxy of 1 to 3 carbon atoms.

One group of preferred compounds is that where X is oxygen, particularly those compounds where n is 1. Preferably, R is hydrogen and $R_1$, $R_2$ and $R_3$ are each selected from hydrogen, chloro, bromo and fluoro. Especially preferred of these compounds are those where $R_2$ and $R_3$ are each hydrogen, including those where $R_1$ is either hydrogen, chloro, bromo or fluoro, most preferably where $R_1$ is chloro. Also preferred are compounds where $R_1$ is chloro, $R_2$ is hydrogen and $R_3$ is chloro and where $R_1$ is chloro, $R_2$ is hydrogen and $R_3$ is methyl.

A further group of compounds of interest is that where X is sulfur, especially where n is 1. Preferably R is hydrogen and $R_1$, $R_2$ and $R_3$ are each selected from hydrogen, chloro, bromo and fluoro. Especially preferred are compounds where $R_2$ and $R_3$ are each hydrogen, including those where $R_1$ is either hydrogen, chloro or fluoro.

Also within the scope of the present invention are intermediates useful for the preparation of the spiro-oxazolidindiones of formula I. Thus, the present invention includes compounds of the formula

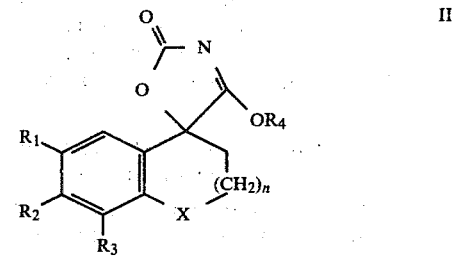

wherein $R_1$, $R_2$, $R_3$, X and n are as previously defined, and $R_4$ is selected from alkyl of 1 to 4 carbon atoms, benzyl and monosubstituted benzyl, wherein said substituent is selected from chloro, bromo, fluoro, hydroxy, alkyl of 1 to 3 carbon atoms and alkoxy of 1 to 3 carbon atoms.

Further intermediates of the present invention are those compounds of the formula

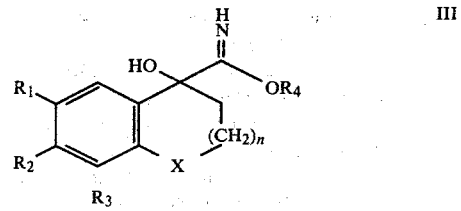

wherein $R_1$, $R_2$, $R_3$, $R_4$, X and n are as previously defined.

Preferred compounds of formulae II and III are those useful for the preparation of the preferred spiro-oxazolidindiones of this invention, as previously described herein i.e. those having the corresponding preferred values for $R_1$, $R_2$, $R_3$, X and n. Preferably, $R_4$ is alkyl of 1 to 3 carbon atoms, most preferably ethyl.

Further intermediates of the present invention are those of the formula

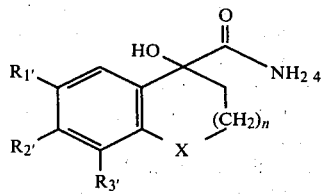

IV wherein X and n are as previously defined and $R_1'$, $R_2'$ and $R_3'$ are each selected from hydrogen, chloro and alkyl of 1 to 3 carbon atoms. A preferred group of compounds is that wherein X is oxygen, n is 1, and $R_1'$, $R_2'$ and $R_3'$ are each hydrogen, chloro or methyl. Of these, preferred compounds are those wherein $R_1'$ is chloro and $R_2'$ and $R_3'$ are each hydrogen, and wherein $R_1'$ and $R_3'$ are each chloro and $R_2'$ is hydrogen. A preferred compound of the group where X is sulfur and n is 1 is that where $R_1'$ is chloro and $R_2'$ and $R_3'$ are each hydrogen.

The present invention further comprises a novel method for the treatment of a diabetic host to prevent or alleviate diabetes-associated complications, such as cataracts, neuropathy or retinopathy, which method comprises administering to the host an effective amount of a compound of formula I.

Also embraced by the present invention is a pharmaceutical composition comprising a pharmaceutically acceptable carrier and a compound of formula I in an amount effective to prevent or alleviate diabetes-associated complications, such as cataracts, neuropathy or retinopathy.

DETAILED DESCRIPTION OF THE INVENTION

The novel spiro-oxazolidindiones of formula I are prepared from appropriately substituted ketones of the formula

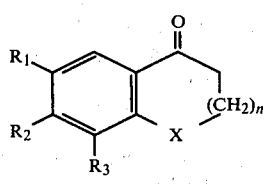

V where $R_1$, $R_2$, $R_3$, X and n are as previously defined. Such compounds are readily available or may be synthesized by conventional routes.

The reaction sequence for formation of compounds of formula I is shown in reaction scheme A, to which reference is made for the following discussion. By way of exemplification, the nomenclature used in the following discussion refers to compounds wherein n is 1. However, it will be understood that the analogous compounds wherein n is 2 will also be formed by the reactions described hereinafter from the appropriate ketone starting material. The ketone 1a is first reacted with trialkylsilyl cyanide, $(R')_3SiCN$, to form the 4-cyano-4-trialkylsilyloxy derivative 2a. A preferred trialkylsilyl cyanide for use in this reaction is trimethylsilyl cyanide, although other lower trialkylsilyl cyanides having from 1 to 4 carbon atoms in each alkyl group may be employed.

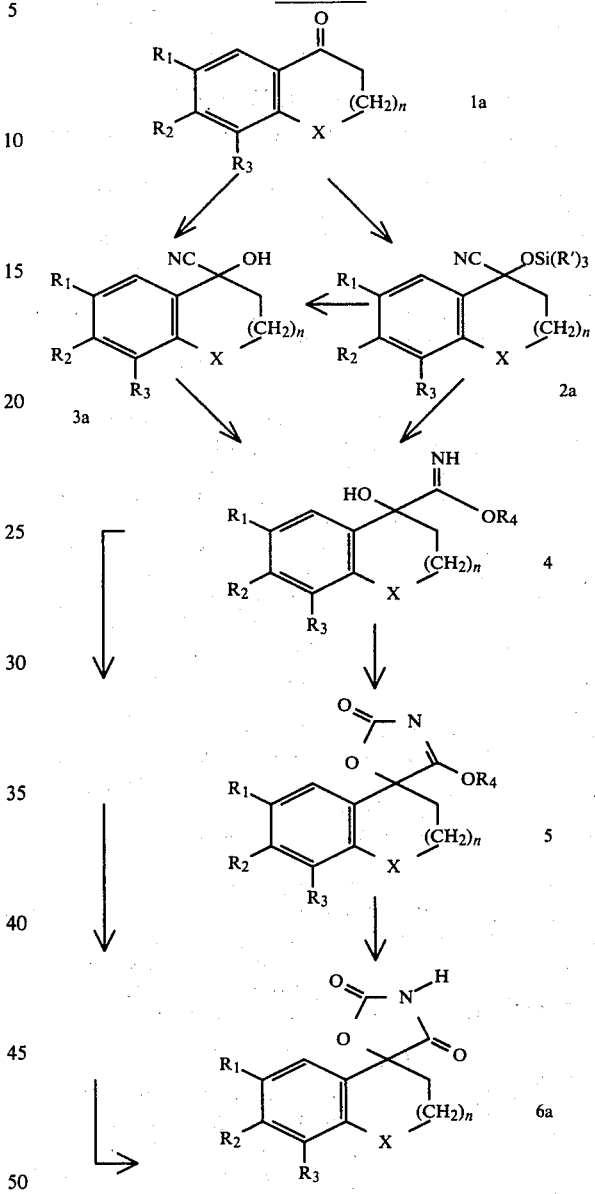

Scheme A

The reaction is conducted in the presence of a Lewis acid catalyst, such as a zinc halide, aluminum halide or boron trifluoride, with zinc iodide being a preferred catalyst. Temperatures in the range of about 0° C. to about 50° C. are generally employed, preferably about 0° C. to 20° C., in an inert organic solvent, typically an ether such as diethyl ether, dimethoxyethane, tetrahydrofuran, dioxane and the like. Compound 2a is then converted to an alkyl 4-hydroxy-4-carboximidate derivative 4 by reaction with an acid in an alcohol solvent $R_4OH$. Suitable acids include hydrogen halides, especially hydrogen chloride. The alcohol $R_4OH$ may be either a lower alkanol of 1 to 4 carbon atoms, benzyl alcohol or a substituted benzyl alcohol, the substituent including chloro, bromo, fluoro, hydroxy, alkyl of 1 to 3 carbon atoms and alkoxy of 1 to 3 carbon atoms. The reaction is generally conducted at temperatures in the cal isomer obtained by the resolution methods described above is first treated with a base, such as an alkali metal hydroxide, such as sodium or potassium hydroxide, at about 0° to 100° C. in a solvent such as water, an alcohol, an ether, for example dioxane, or mixtures thereof. The spiro-oxazolidindione is thereby converted to the precursor 4-hydroxy-carboxamide (formula 7 shown in reaction Scheme B) of the same configuration as the initial spiro-oxazolidindione. This carboxamide 7 is then reacted with a dialkylazodicarboxylate, such as diethylazodicarboxylate or other lower alkyl analogues thereof in the presence of a trivalent phosphorous compound such as a triaryl phosphine, for example triphenyl phosphine, and a carboxylic acid such as formic acid or benzoic acid. The reaction is generally conducted at about 0° to 150° C. in an inert organic solvent such as tetrahydrofuran. The product from this reaction is the ester of the corresponding epimeric 4-hydroxy-carboxamide i.e. the formate or benzoate esters of the carboxamide of formula 7 epimerized at the 4-position. The ester group is then hydrolyzed by treatment with a base such as an alkali metal hydroxide to form the 4-hydroxy-carboxamide of formula 7 epimerized at the 4-position i.e. of opposite configuration to the initial resolved spiro-oxazolidindiones. The epimerized 4-hydroxy-carboxamide is then converted to the epimer of the initial spiro-oxazolidindiones by the methods described previously for the conversion of 7 to 6b. Racemization may occur to some extent during the above sequence of reactions. The desired optical isomer may then be obtained by employing the resolution methods previously described. By use of the above method, a spiro-oxazolidindione isomer of preferred activity as an aldose reductase inhibiting agent may be obtained from the corresponding epimer. Thus, for example, the 1-isomers of 6-chloro-spiro-[4H-2,3-dihydrobenzopyran(4,5-')oxazolidin]-2',4'-dione and 6,8-dichloro-spiro[4H-2,3-dihydrobenzopyran(4,5')oxazolidin]-2',4'-dione may be obtained from the corresponding d-isomers.

The novel spiro-oxazolidin-2,4-diones of this invention are useful as aldose reductase inhibitors, and as such are of therapeutic value in the treatment of chronic complications of diabetes, such as cataracts, retinopathy and neuropathy. As used in the claims and specification hereof, treatment is meant to include the prevention or alleviation of such conditions. The compounds may be administered to a subject in need of treatment by a variety of conventional routes of administration, including orally and parenterally. In general these compounds will be administered at doses between about 1 and 500 mg per kg. body weight of the subject to be treated per day, preferably at about 1 to 25 mg/kg per day. However, some variation in dosage will necessarily occur depending on the condition of the subject being treated and the particular compound employed and the physician will, in any event, determine the appropriate dose for the individual subject.

The compounds may be administered alone or in combination with pharmaceutically acceptable carriers, in either single or multiple doses. Suitable pharmaceutical carriers include inert solid diluents or fillers, sterile aqueous solutions and various non-toxic organic solvents. The pharmaceutical compositions formed by combining a spiro-oxazolidin-2,4-dione and the pharmaceutically acceptable carrier are then readily administered in a variety of dosage forms such as tablets, powders, lozenges, syrups, injectable solutions and the like. These pharmaceutical compositions can, if desired, contain additional ingredients such as flavorings, binders, excipients and the like. Thus for purposes of oral administration, tablets containing various excipients such as sodium citrate, calcium carbonate and calcium phosphate may be employed along with various disintegrants such as starch, preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules; preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and if desired, emulsifying or suspending agents, together with diluents such as water, ethanol, propylene glycol, glycerin and combinations thereof.

For parenteral administration, solutions of the spiro-oxazolidin-2,4-diones in sesame or peanut oil or in aqueous propylene glycol may be employed, as well as sterile aqueous solutions of the corresponding water-soluble alkali metal or alkaline earth metal salts previously described. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well known to those skilled in the art. Additionally, it is also possible to administer a spiro-oxazolidin-2,4-diones topically, by use of an appropriate opthalmic solution, which may then be administered dropwise to the eye.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve of acutely streptozotocinized (i.e. diabetic) rats; (3) measuring their ability to reverse already elevated sorbitol levels in the sciatic nerve and lens of chronic streptozotocin-induced diabetic rats; (4) measuring their ability to prevent or inhibit galactitol formation in the lens of acutely galactosemic rats; and (5) measuring their ability to delay cataract formation and reduce the severity of lens opacities in chronic galactosemic rats. Suitable experimental procedures are described in U.S. Pat. No. 3,821,383 and the references cited therein.

The present invention is illustrated by the following examples. It will be understood, however, that the invention is not limited to the specific details of these examples.

EXAMPLE 1

6-Chloro-4-cyano-4-trimethylsilyloxy-4H-2,3-dihydrobenzopyran

A mixture of 6-chloro-4H-2,3-dihydrobenzopyran-4-one (20.0 g, 0.11 mol, Aldrich), trimethylsilyl cyanide (13.0 g, 0.13 mol, Silar), and zinc iodide (0.2 g in Alfa) in 50 ml ether was stirred for 18 hours. The solution was decolorized with charcoal (Darco), filtered, and evaporated in vacuo to an orange oil which on addition of pentane gave crystalline 6-chloro-4-cyano-4-trimethylsilyloxy-4H-2,3-dihydrobenzopyran, 26.4 g (84%), m.p. 67°–69° C.

EXAMPLE 2

Ethyl 6-chloro-4-hydroxy-4H-2,3-dihydrobenzopyran-4-carboximidate

A saturated solution of 6-chloro-4-cyano-4-trimethylsilyloxy-4H-2,3-dihydrobenzopyran (273.0 g, 0.97 mol) in 2.0 l of ethanol was cooled to 0° C. and perfused with dry hydrogen chloride for 40 minutes. A slight exotherm occurred while the mixture became homogeneous. After 16 hours at 4° C. the volatiles were removed in vacuo yielding a semi-solid residue. Trituration with 800 ml diethyl ether followed by filtration afforded a solid which was partitioned between 3.8 l of chloroform and 500 ml saturated sodium bicarbonate. The organic layer was washed with an additional 500 ml saturated sodium bicarbonate, dried over magnesium sulfate, filtered, and evaporated in vacuo to solid ethyl 6-chloro-4-hydroxy-4H-2,3-dihydrobenzopyran-4-carboximidate, 193.0 g (78%). Trituration with ether afforded material of mp 124°–126° C.

EXAMPLE 3

6-chloro-spiro[4H-2,3-dihydrobenzopyran(4,5')oxazolidin]2',4'-dione

A mixture of ethyl 6-chloro-4-hydroxy-4H-2,3-dihydrobenzopyran-carboximidate, (500 g, 1.95 mol) and triethylamine (400 g, 3.96 mol) in 13 l of dry tetrahydrofuran at 5° C. was perfused with phosgene (1818 g, 18.4 mol) at such a rate as to maintain the temperature below 27° C. Stirring was continued during the perfusion and concomitant precipitate formation. After perfusion the temperature was allowed to come to 20° C. and maintained there for 48 hours. Analysis by Thin Layer Chromatography showed a spot at Rf=0.57 with no spot at Rf=0.29 present (1:1 chloroform:ethyl acetate on silica gel). (Material with Rf=0.29 is the starting imidate while the material at Rf=0.57 is the intermediate ethoxy oxazolin-2'-one of Example 6 described hereinafter). The mixture was then poured into 13 l of cracked ice with stirring, phosgene and carbon dioxide being liberated. The two-phase mixture was neutralized with 50% sodium hydroxide (1.7 l) to pH 7. Sodium carbonate (248 g, 2.0 mol) was then added and the mixture was stirred for 16 hours at 20° C. The product was isolated by the following extraction procedure: Ethyl acetate (12 l) was added to the mixture and, after shaking, the aqueous layer was collected. The organic phase was washed twice with 12 l of 7% sodium bicarbonate. The combined aqueous layers were acidified to pH 1 with cooling (10°–15° C.) by addition of concentrated hydrochloric acid. The aqueous layer was extracted three times with 12 l ethyl acetate. The combined organic phase was washed with 12 l saturated sodium chloride, dried over magnesium sulfate, filtered, and evaporated in vacuo to solid; 392 g (79%), mp 191°–195° C. Recrystallization from toluene gave 6-chloro-spiro[4H-2,3-dihyrobenzopyran(4,5')oxazolidin]-2',4'-dione of mp 196°–198° C., Rf=0.44 (1:1 CHCl₃:EtOAc on silicic acid).

EXAMPLE 4

6-Chloro-spiro[4H-2,3-dihydrobenzopyran(4,5')oxazolidine]-2',4'-dione

A mixture of the ethyl 6-chloro-4-hydroxy-4H-2,3-dihydrobenzopyran-4-carboximidate (5.0 g, 0.019 mol) and 1,1'-carbonyl diimidazole (Aldrich, 3.7 g, 0.023 mol) was heated in dioxane (5 ml) at 90° C. for 16 hours. Analysis of the reaction mixture by Thin Layer Chromatography after 1 hour showed a spot Rf=0.57 (1:1 chloroform:ethyl acetate on silicic acid) which corresponded to the ethoxy oxazolin-2'-one of Example 6 described hereinafter. After cooling the mixture was diluted with 100 ml ethyl acetate and washed twice with 100 ml 1 N hydrochloric acid. The organic layer was extracted twice with 100 ml saturated sodium bicarbonate. The basic layer was acidified with 6 N hydrochloric acid to pH 1 and extracted three times with 100 ml ethyl acetate. This latter organic phase washed with brine, dried over magnesium sulfate, filtered, and evaporated in vacuo to a solid; 1.20 g (25%), mp 189°–191° C. Recrystallization from toluene gave 6-chlorospiro[4H-2,3-dihydrobenzopyran(4,5')oxazolidine]-2',4'-dione with mp 192°–193° C.

EXAMPLE 5

6-Chloro-spiro[4H-2,3-dihydrobenzopyran(4,5')oxazolidine]-2',4'-dione

A mixture of ethyl chloroformate (2.00 g, 2.82 mol), ethyl-6-chloro-4-hydroxy-4H-2,3-dihydrobenzopyran-4-carboximidate (1.69 g, 1.56 mmol), and 5 ml pyridine were reacted at 0° C. for 1 hour then warmed to room temperature and finally refluxed for 4 hours. Concentration in vacuo and extraction as described in Example 3 afforded the 6-chloro-spiro[4H-2,3-dihydrobenzopyran (4,5')oxazolidine]-2',4'-dione in 10% yield; mp 195°–198° C.

EXAMPLE 6

6-Chloro-4'-ethoxy-spiro[4H-2,3-dihydrobenzopyran(4,5')oxazolin]-2'-one

A solution of ethyl 6-chloro-4-hydroxy-4H-2,3-dihydrobenzopyran-4-carboximidate (1.15 g, 4.00 mmol) in 60 ml tetrahydrofuran was cooled to 0° C. and stirred while phosgene was infused for 5 minutes. After 30 minutes, thin layer chromatography analysis of the reaction showed a new spot at Rf=0.57 (1:1 chloroform:ethyl acetate acetate on silicic acid) with no starting imidate, Rf=0.29, present. The mixture was poured onto 90 ml ice/water and extracted twice with 50 ml ethyl acetate. The organic layer was washed twice with 30 ml 5% sodium bicarbonate, dried over magnesium sulfate, filtered and evaporated in vacuo to an oil (0.651 g) which was crystallized at low temperature from ether/hexane; 0.350 g (31%) mp 108°–110° C. This ethoxy oxazoline was also prepared from the imidate using ethyl chloroformate in pyridine in 62% yield.

EXAMPLE 7

6-Chloro-spiro[4H-2,3-dihydrobenzopyran(4,5')oxazolidin]2',4'-dione

A mixture of 6-chloro-4'-ethoxy-spiro[4H-2,3-dihydrobenzopyran(4,5')oxazolin]-2'-one (100 mg, 0.355 mmol) and sodium carbonate (88 mg, 0.710 mmol) in 2 ml 1:1 tetrahydrofuran:water were stirred at 20° C. for 16 hours. After addition of 10 ml ethyl acetate and 10 ml range of about −10° C. to about 25° C., preferably at about 0° C. to 10° C.

The 4-hydroxy-4-carboximidate derivative 4 may also be prepared from the ketone starting material 1a via the cyanohydrin derivative 3a. The latter is formed by reaction of the ketone with liquid hydrogen cyanide, in the presence of a base such as piperidine, pyridine and the like, at a temperature of about 0° C. to 50° C., preferably at about 0° C. to 10° C. following the procedure described by Stoughton, J.A.C.S. 63, 2376 (1941). The cyanohydrin is then converted to the 4-hydroxy-4-carboximidate derivative 4 using a hydrogen halide in alcohol solvent, as previously described for the conversion of 2a to 4.

The cyanohydrin 3a may also be formed from the 4-cyano-4-trialkylsilyloxy derivative 2a and may be isolated as an intermediate during the initial stages of the conversion of 2a to 4 by reaction with a hydrogen halide and an appropriate alcohol, as previously described.

The 4-hydroxy-4-carboximidate derivative 4 may be converted directly to the spiro-oxazolidin-2,4-dione 6a by a number of methods. In all cases, the spiro-oxazolin-2-one 5 is an intermediate and can, if desired, be isolated from the reaction mixture. However, it is generally preferred to convert 4 to 6a directly without such isolation of the intermediate 5. The 4-hydroxy-4-carboximidate may be reacted with phosgene in the presence of a base such as triethylamine, or other trialkylamines having from 1 to 4 carbon atoms in each alkyl group, in an inert organic solvent such as an ether, for example diethyl ether, tetrahydrofuran, dimethoxyethane, dioxane and the like. The phosgene is generally bubbled through the reaction solution at a temperature of about −10° C. to about 10° C., for about 15 to 75 minutes and the solution is subsequently stirred at about 20° C. to 50° C., preferably at room temperature for about 12 to 48 hours, when the spiro-oxazolin-2-one 5 is predominantly formed. This intermediate may then be converted to the desired spiro-oxazolidin-2,4-dione 6a either by a further perfusion of phosgene at about −10° C. to about 10° C. for about 15 to 75 minutes, followed by stirring at room temperature for a further period of about 12 to 48 hours. Alternatively, an alkali metal carbonate, such as potassium or sodium carbonate, or ammonium carbonate can be added to the solution of the intermediate 5 and stirred at a temperature of about 15° C. to about 50° C., preferably at about room temperature, for a period of about 6 to 24 hours to form the desired spiro-oxazolidin-2,4-dione.

The desired spiro-oxazolidin-2,4-dione can also be prepared from the 4-hydroxy-4-carboximidate derivative 4 by reaction with an alkyl haloformate, where the alkyl group is of 1 to 4 carbon atoms, a preferred reagent being ethyl chloroformate. The reaction is generally conducted by stirring the intermediate 4, together with the alkyl haloformate in an inert solvent, such as pyridine, at a temperature of about −10° C. to about 15° C., preferably at about 0° C. for a period of about 30 minutes to about 2 hours, followed by heating the solution to a higher temperature, about 50° C. to about 150° C., preferably about 90° C. to 120° C., for example to reflux temperature in pyridine, for about 2 to about 6 hours. If desired the spiro-oxazolin-2-one intermediate 5 can be isolated from the initial reaction mixture after heating the solution for relatively shorter periods, for example about 1 hour.

The spiro-oxazolidin-2,4-diones can also be prepared from the intermediate 4 by reaction with 1,1'-carbonyldiimidazole, the reaction being generally conducted at a temperature of about 50° C. to 150° C., preferably about 80° C. to 110° C., neat or in an inert organic solvent such as dioxane, tetrahydrofuran, dimethoxyethane, dimethyl ether and the like, for a period of about 12 to 36 hours. If desired, the intermediate spiro-oxazolin-2-one 5 can be obtained by heating for only a relatively short period of time, for example about 30 minutes to about 90 minutes.

An alternative method of preparation available for certain of the substituted spiro-oxazolidin-2,4-diones of this invention is illustrated in reaction scheme B, to which reference is made for the following discussion. By way of exemplification, the nomenclature used in the following discussion refers to compounds wherein n is 1. However, it will be understood that the analogous compounds wherein n is 2 will also be formed by the reactions described hereinafter from the appropriate ketone starting material. Starting materials are ketones of the formula 1b, wherein $R_1'$, $R_2'$ and $R_3'$ are selected from hydrogen, chloro and alkyl of 1 to 3 carbon atoms and X and n are as previously defined.

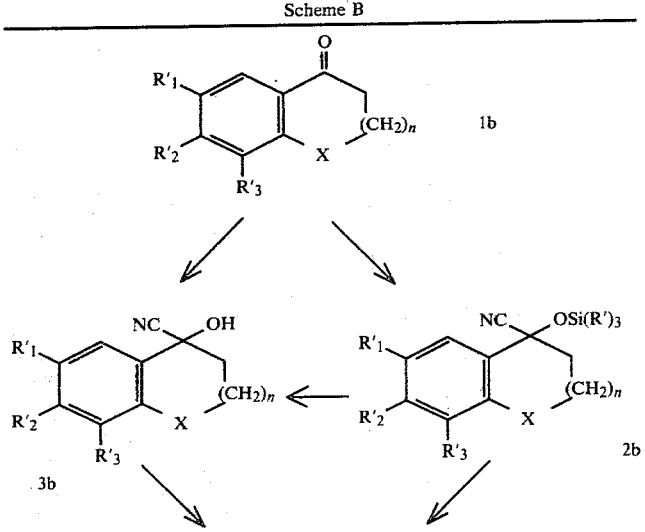

Scheme B

Scheme B

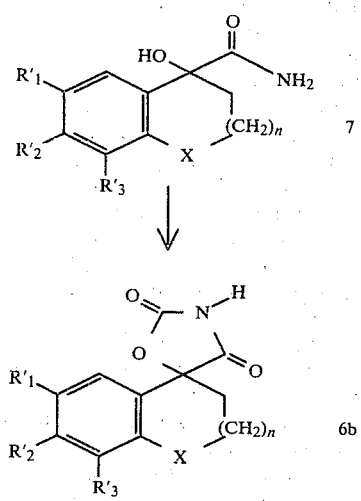

The first step is the formation of either the 4-cyano-4-trimethylsilyloxy derivative 2b or the cyanohydrin 3b using the reaction conditions and reagents previously described for the conversion of 1a to 2and 3a, respectively. The intermediates 2b and 3b are converted to the amide 7 by treatment with acid such as concentrated hydrochloric or sulfuric acid in aqueous solution at a temperature between about 0° C. to about 30° C. For example, the reaction may be conducted by bubbling dry hydrogen chloride through a solution of either 2b or 3b in concentrated hydrochloric acid at about 0° C. to 5° C. for about 5 to 30 minutes, followed by stirring at about 15° C. to 30° C. for a period of about 6 to 24 hours.

The amide 7 may be converted to the desired spirooxazolidin-2,4-dione 6b by reaction with a dialkyl carbonate, such as diethyl carbonate, in the presence of an alkali metal alkoxide, for example sodium t-butoxide or potassium t-butoxide in a normal alkanol solvent having from 1 to 6 carbon atoms, for example n-butanol. The reaction is generally conducted by heating the mixture at about 70° C. to 150° C., preferably at about 100° C. to 125° C. for about 12 to 72 hours.

The amide 7 may also be converted to the desired spiro-oxazolidin-2,4-dione by reaction with ethyl chloroformate by procedures analogous to those described in Stoughton, J.A.C.S. 63, 2376 (1941).

Production of compounds of formula I wherein R is alkyl, benzyl or substituted benzyl is effected by further reacting those compounds where R is hydrogen to introduce the desired substituent, using alkylation reactions well known in the art. Such compounds may also be prepared by similar reaction of the 4-hydroxy-4-carboximidate 4 of reaction scheme A to form a corresponding N-alkyl or N-benzyl substituted compound, followed by conversion to the N-substituted spiro-oxazolidin-2,4-dione, as described for the conversion of 4 to 6a.

Spiro-oxazolidin-2,4-diones of this invention formed as described above can be readily isolated from the reaction medium by conventional means, for example by evaporation of the solvent followed by extraction with ether and chloroform and recrystallization from toluene or a similar aromatic solvent.

Pharmaceutically acceptable salts can be readily prepared from compounds of formula I wherein R is hydrogen by conventional methods. Thus, these salts may be readily prepared by treating such spiro-oxazolidin-2,4-diones with an aqueous solution of the desired pharmaceutically acceptable cation and evaporating the resulting solution to dryness, preferably under reduced pressure. Alternatively, a lower alkanoic solution of the spiro-oxazolidin-2,4-dione may be mixed with an alkoxide of the desired metal and subsequently evaporating the solution to dryness. Suitable pharmaceutically acceptable cations for this purpose include, but are not limited to potassium, sodium, ammonium, calcium and magnesium.

It will be understood that the novel spiro-oxazolidin-2,4-diones of this invention contain an asymmetric center and thus will exhibit optical isomerism. If desired, the racemic spiro-oxazolidin-2,4-dione formed by the methods previously described can be resolved into the d- and l-isomeric forms by the application of conventional resolution methods. For example, cinchonidine can be employed to selectively form an adduct with the (+)-isomer, for example, of 6-chloro-spiro-[4H-2,3-dihydrobenzopyran (4,5')oxazolidin]-2',4'-dione. The (+)-isomer can then be readily obtained from the isolated adduct, for example by treatment with a mineral acid, such as hydrochloric acid, and extraction with a suitable organic solvent, such as ethyl acetate and the like. The (−)-isomer also can be obtained from the mother liquor after removal of the adduct formed selectively with the (+)-isomer. The (−)-isomer can also be obtained by formation of an adduct with l-amphetamine, followed by subsequent reaction of the adduct with acid to obtain the free isomer. The l-isomers (i.e. the isomers having negative optical rotation), of 6-chloro-spiro[4H-2,3-dihydrobenzopyran(4,5')oxazolidin]-2',4'-dione and 6,8-dichloro-spiro[4H-2,3-dihydrobenzopyran(4,5')oxazolidin]-2',4'-dione are of particular interest as aldose reductase inhibiting compounds.

If desired an optical isomer of either the d- or l-configuration may be converted to its corresponding epimer by methods analogous to those described by A. K. Bose, Tetrahedron Letters, 1973, 1619. Thus, the optiwater the extraction as described in Example 3 afforded 6-chloro-spiro[4H-2,3-dihydrobenzopyran(4,5')oxazolidin]2',4'-dione, 63 mg (70%9, mp 192°-195° C.

EXAMPLE 8

6-Chloro-4-hydroxy-4H-2,3-dihydrobenzopyran-4-carboxamide

A mixture of 6-chloro-4-cyano-4-trimethylsilyloxy-4H-2,3-dihydrobenzopyran (1.40 g, 5.0 mmol) and 3 ml of concentrated hydrochloric acid was perfused at 0° C. with dry hydrogen chloride gas for 5 minutes. The mixture never became homogeneous even after 23 hours at 20° C. The mixture was diluted with 30 ml each of water and ethyl acetate. The organic layer was washed twice with 50 ml saturated sodium chloride dried over magnesium sulfate, filtered, and evaporated in vacuo to a residue which after trituration with methylene chloride gave 6-chloro-4-hydroxy-4H-2,3-dihydrobenzopyran-4-carboxamide; 0.606 g (54%), mp 168°-169° C., Rf=0.18 (1:1 chloroform:ethyl acetate, silicic acid).

EXAMPLE 9

6-Chloro-spiro[4H-2,3-dihydrobenzopyran(4,5')oxazolidin]-2',4'-dione

Sodium (0.101 g, 4.40 mmol) was reacted with n-butanol (3.34 g, 44.0 mmol) and diethyl carbonate (0.545 g, 4.62 mmol). After hyrogen evolution ceased, 6-chloro-4-hydroxy-4H-2,3-dihydrobenzopyran-4-carboxamide (1.00 g, 4.40 mmol) was added and the mixture heated at 115° C. for 3 days. Further addition of diethyl carbonate (0.545 g, 4.62 mmol) and potassium tert-butoxide (Aldrich, 0.100 g, 0.89 mmol) with 4 days more heating led to completion of the reaction. The cooled mixture was poured onto 100 ml of ice cold 1 N hydrochloric acid. The aqueous layer was extracted twice with 100 ml ethyl acetate. The combined organic phase was extracted twice with 50 ml of 5% sodium bicarbonate. The basic phase was acidified with 6 N hydrochloric acid and extracted twice with 100 ml of ethyl acetate. This organic layer was dried over magnesium sulfate, filtered, and evaporated in vacuo to a solid. Recrystallization from toluene yielded 6-chloro-spiro[4H-2,3-dihydrobenzopyran(4,5')oxazolidin]-2',4'-dione, 0.299 g (27%) mp 190°-193° C.

EXAMPLES 10-17

In like manner to that described in Example 1, the following compounds were prepared by using the appropriate ketones in place of 6-chloro-4H-2,3-dihydrobenzopyran-4-one. All compounds were isolated as oils after washing with 5% sodium bicarbonate and brine and drying over magnesium sulfate followed by evaporation in vacuo. Characterization was accomplished with NMR and/or thin layer chromatography on silicic acid.

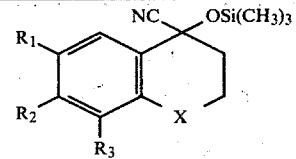

| Example No. | $R_1$ | $R_2$ | $R_3$ | X | Rxn Time | (%) Yield | Rf (solvent) |
|---|---|---|---|---|---|---|---|
| 10 | Br | H | H | O | 16 hr | Quant. | 0.90 (diethyl ether) |
| 11 | F | H | H | O | 16 hr | 99 | 0.79 (diethyl ether) |
| 12 | Cl | H | Cl | O | 72 hr | 89 | 0.90 (ethyl acetate) (mp 68-71° C.) |
| 13 | Cl | H | $CH_3$ | O | 24 hr | 58* | 0.90 (ethyl acetate) |
| 14 | F | H | H | S | 18 hr | Quant. | — |
| 15 | Cl | H | H | S | 72 hr | 98.6 | 0.89(diethyl ether:pentane) |
| 16 | H | H | H | S | 72 hr | 99 | 0.77(diethyl ether:pentane) |
| 17 | H | H | H | O | 18 hr | Quant. | — |

*Determined by NMR

EXAMPLES 18-23

In like manner to that described in Example 2, the following compounds were prepared by using the appropriate reactants in place of 6-chloro-4-cyano-4-trimethylsilyloxy-4H-2,3-dihydrobenzopyran, except that the following modified work-up was used. The crude mixture was partitioned between water and ethyl acetate and the layers separated. The aqueous phase was basified with 6 N sodium hydroxide to pH 12 and extracted with ethyl acetate. This organic phase was washed with brine, dried over magnesium sulfate, filtered, and evaporated in vacuo to give the solid imidates.

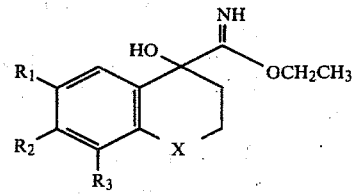

| Example No. | $R_1$ | $R_2$ | $R_3$ | X | Rxn (Perfusion) | (%) Yield | M.P. |
|---|---|---|---|---|---|---|---|
| 18 | F | H | H | O | 4 hr[a] (30 min) | 69 | 118.5-20° |
| 19 | Br | H | H | O | 18 hr[a] (20 min) | 23 | 117-122° |
| 20 | H | H | H | S | 18 hr[b] (15 min) | 65 | 145-147° |
| 21 | F | H | H | S | 18 hr (15 min) | 44 | 139-40.5° (diethyl ether: hexane) |
| 22 | Cl | H | Cl | O | 48 hr (30 min) | 59 | 125.5-129° (hexane) |
| 23 | H | H | H | O | 18 hr[b] (30 min) | 86 | 98-101° |

[a]Left at room temperature (20° C.)
[b]Refrigerated to 4° C.

EXAMPLES 24-26

In a like manner to that described in Example 8, the following compounds were prepared using the appropriate reactants in place of 6-chloro-4-cyano-4-trimethylsilyloxy-4H-2,3-dihydrobenzopyran.

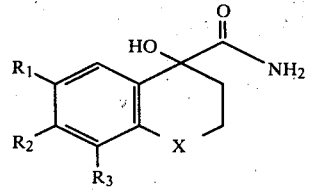

| Example No. | R₁ | R₂ | R₃ | X | Perfusion Time | (%) Yield | M.P. |
|---|---|---|---|---|---|---|---|
| 24 | Cl | H | CH₃ | O | 1 min | 37 | 157–159° C. |
| 25 | Cl | H | Cl | O | 10 min | 83 | 200–200.5°C. |
| 26 | Cl | H | H | S | 60 min | 68 | 121–123° C. |

EXAMPLE 27

Spiro[4H-2,3-dihydrobenzopyran(4,5')oxazolidin]-2',4'-dione

A mixture of ethyl 4-hydroxy-4H-2,3-dihydrobenzopyran-4-carboximidate (5.50 g, 24.9 mmol) and triethyl amine (5.03 g, 49.7 mmol) in 50 ml tetrahydrofuran at 0° was saturated with phosgene gas for 30 minutes. A solid immediately formed during perfusion. The mixture was stirred for 16 hours at 20° C. Under these conditions the oxazolidindione is obtained directly without isolation and hydrolysis of the intermediate oxazoline. The reaction mixture is poured onto 200 ml of cracked ice and extracted with ethyl acetate. Spiro [4H-2,3-dihydrobenzopyran(4,5')oxazolidin]-2',4'-dione was isolated from this organic phase by the procedures as described in Example 3 in 56.7% yield; mp 168°–170° C.

EXAMPLE 28

6-Fluoro-spiro[4H-2,3-dihydrobenzopyran(4,5')oxazolidin]-2',4'-dione

6-Fluoro-spiro[4H-2,3-dihydrobenzopyran(4,5')oxazolidin]-2',4'-dione was prepared in a like manner to that described in Example 4 from ethyl 6-fluoro-4-hydroxy-4H-2,3-dihydrobenzopyran-4-carboximidate in 43% yield, except that the mixture was heated at 100° C. for 1.0 hour; mp 177.5°–180° C. after recrystallization from toluene.

EXAMPLE 29

6-Bromo-spiro[4H-2,3-dihydrobenzopyran(4,5')oxazolidin]-2',4'-dione

6-Bromo-spiro[4H-2,3-dihydrobenzopyran(4,5')oxazolidin]-2',4'-dione was prepared in a like manner to that described in Example 4 from ethyl 6-bromo-4-hydroxy-4H-2,3-dihydrobenzopyran-4-carboximidate in 38% yield, except that the mixture was heated at 100° C. for 0.5 hour; mp 188°–191° C. after recrystallization from toluene.

EXAMPLE 30

Spiro[4H-2,3-dihydrobenzothiopyran(4,5')oxazolidin]-2',4'-dione

Spiro[4H-2,3-dihydrobenzothiopyran(4,5')oxazolidin]-2',4'-dione was prepared in a like manner to that described in Example 4 from ethyl-4-hydroxy-4H-2,3-dihydrobenzothiopyran-4-carboximidate in 45% yield, except that the mixture was heated at 100° C. for 7.0 hours, mp 165°–167° C. after recrystallization from toluene.

EXAMPLE 31

6-Fluoro-spiro[4H-2,3-dihydrobenzothiopyran(4,5')oxazolidin]-2',4'-dione

6-Fluoro-spiro[4H-2,3-dihydrobenzothiopyran(4,5-')oxazolidin]-2',4'-dione was prepared in a like manner to that described in Example 4 from ethyl-6-fluoro-4-hydroxy-4H-2,3-dihydrobenzothiopyran-4-carboxamidate in 41% yield, except that the mixture was heated at 100° C. for 48 hours, mp 193°–194.5° C. after recrystallization from toluene.

EXAMPLE 32

6,8-Dichloro-spiro[4H-2,3-dihydrobenzopyran(4,5')oxazolidin]-2',4'-dione

A mixture of 6,8-dichloro-4-hydroxy-4-carboxamide (524 mg, 2.00 mmol), ethyl carbonate (531 mg, 4.5 mmol), potassium tert-butoxide (396 mg, 2.67 mmol, Aldrich), and 1.80 ml of n-butanol were refluxed for 64 hours. The reaction mixture was quenched with 100 ml 1 N sulfuric acid and 100 ml ethyl acetate. The aqueous phase was washed with another 100 ml ethyl acetate and the combined organic layers were then extracted twice with 50 ml, 5% sodium bicarbonate. The basic phase was acidified with 6 N hydrochloric acid and extracted twice with 75 ml ethyl acetate. This latter combined organic phase was washed with 50 ml brine, dried over magnesium sulfate, filtered and evaporated in vacuo to a solid; 330 mg (57%). Recrystallization of this from toluene gave 6,8-dichloro-spiro[4H-2,3-dihydrobenzopyran(4,5')oxazolidin]-2',4'-dione of mp 193°–195° C.

EXAMPLE 33

6-Chloro-8-methyl-spiro[4H-2,3-dihydrobenzopyran(4,5')oxazolidin]-2',4'-dione

6-Chloro-8-methyl-spiro[4H-2,3-dihydrobenzopyran(4,5')-oxazolidin]-2',4'-dione was prepared in like manner to that described in Example 32 from 6-chloro-8-methyl-4-hydroxy-4H-2,3-dihydrobenzopyran-4-carboxamide in 21.6% yield, mp 185.5°–187° C. after recrystallization from toluene.

EXAMPLE 34

6-Chloro-spiro[4H-2,3-dihydrobenzothiopyran(4,5')oxazolidin]-2',4'-dione

6-Chloro-spiro[4H-2,3-dihydrobenzothiopyran(4,5')-oxazolidin]-2',4'-dione was prepared in like manner to that described in Example 32 from 6-chloro-4-hydroxy-4H-2,3-benzothiopyran-4-carboxamide in 38% yield, except that the reaction mixture was refluxed 54 hours, mp 213°–216° C. after recrystallization from toluene.

EXAMPLE 35

(−)-6-Chloro-spiro[4H-2,3-dihydrobenzopyran(4,5-')oxazolidin]-2',4'-dione

Racemic 6-chloro-spiro[4H-2,3-dihydrobenzopyran(4,5')-oxazolidin]-2',4'-dione (32.0 g, 0.126 mol) and cinchonidine (37.1 g, 0.126 mol) were dissolved with heating in 290 ml anhydrous ethanol. After cooling a solid, the adduct of the (+)-oxazolidindione and cinchonidine was collected by filtration, 28.0 g (81%). The filtrate was concentrated in vacuo to a residue which was partitioned between 500 ml ethyl acetate and 400 ml 1 N hydrochloric acid. The organic layer was washed with an additional 400 ml 1 N hydrochloric acid, 200 ml brine, dried over magnesium sulfate, filtered, and concentrated to 150 ml. To this organic solution was added liquid L-amphetamine (10.13 g, 0.075 mol). The ensuing heavy precipitate was filtered, washed with ether and dried in vacuo to give to the (−)-oxazolidindione-L-amphetamine adduct, 14.85 g (60%), $[\alpha]_D^{EtOH} = -36.29°$, mp 171°–174° C. This adduct (14.80 g) was partitioned between 300 ml ethyl acetate and 200 ml 3 N hydrochloric acid. The organic layer was washed with an additional 200 ml 3 N hydrochloric acid, 100 ml brine, dried over magnesium sulfate, filtered and evaporated in vacuo to a colorless solid; 9.45 g (97.8% recovery), $[\alpha]_D^{EtOH} = -60.58°$, mp 201°–202.5° C. Recrystallization from toluene gave (−)-6-chloro-spiro[4H-2,3-dihydrobenzopyran (4,5')oxazolidin]-2',4'-dione, 8.203 g, mp 200°–200.5° C., $[\alpha]_D^{EtOH} = -61.59°$ C.

EXAMPLE 36

Resolution of 6-chloro-spiro[4H-2,3-dihydrobenzopyran(4,5')-oxazolidin]-2',4'-dione 6-chloro-spiro[4H-2,3-dihydrobenzopyran(4,5')oxazolidin]-2',4'-dione (1.00 g, 3.95 mmol) and cinchonidine (1.16 g, 3.95 mmol) were dissolved in hot ethanol. After the adduct precipitated, it was collected and recrystallized from ethanol, mp 206°–207° C. This solid was partitioned between 50 ml each of ethyl acetate and 1 N hydrochloric acid. The acid phase was extracted with 50 ml ethyl acetate. The combined organic layers were washed with 50 ml brine, dried over magnesium sulfate, filtered and evaporated in vacuo to a residue which was recrystallized from toluene; 288 mg (57%), mp 193°–197° C. Recrystallization of this from toluene gave (+)-6-chloro-spiro[4H-2,3-dihydrobenzopyran(4,5')oxazolidin]-2',4'-dione, 200 mg (40%), mp 200°–201.5° C., $[\alpha]_D^{EtOH}$ (+)60.55°.

From the first ethanol mother liquor was obtained a small second crop of (+)-adduct crystals upon sitting overnight. After filtration, this mother liquor was then partitioned between 50 ml each of 1 N hydrochloric acid and ethyl acetate. The oxazolidindione obtained as above was recrystallized twice from toluene to give 6-chloro-spiro[4H-2,3-dihydrobenzopyran(4,5')oxazolidin]-2',4'-dione, 143 mg (29%), mp 199°–200° C., $[\alpha]_D^{EtOH} = (-)61.72°$ C.

EXAMPLE 37

Resolution of 6-chloro-spiro[4H-2,3-dihydrobenzopyran(4,5')-oxazolidin]-2',4'-dione 6-chloro-spiro[4H-2,3-dihydrobenzopyran(4,5')oxazolidin]-2',4'-dione (1.00 g, 3.95 mmol) and L-amphetamine (264 mg, 2.00 mmol) were dissolved in hot ethyl acetate. The dried crystals collected after cooling 419 mg, mp 165°–168° C., were recrystallized from ethyl acetate; 221 mg, mp 171°–173° C., $[\alpha]_D^{EtOH}$ (−)32.7° C. The cleavage of the adduct and isolation of the (−) oxazolidindione was achieved as described in Example 33; 53 mg, mp 198°–200° C., $[\alpha]_D^{EtOH}$ (−)60.83° C.

EXAMPLE 38

Spiro-oxazolidindiones prepared as described in the previous examples were tested for their ability to reduce or inhibit aldose reductase enzyme activity, following the procedure described in U.S. Pat. No. 3,821,383 and based on the procedure of Hayman et. al., Journal of Biological Chemistry, 240, 877 (1965). The substrate employed was partially purified aldose reductase enzyme obtained from calf lens. The results obtained with each compound at a concentration of $10^{-6}$ M are expressed as percent inhibition of enzyme activity.

| Compound of | % Inhibition at $10^{-6}$M |
|---|---|
| 3 | 86/68 |
| 28 | 65 |
| 29 | 100/87 |
| 30 | 42 |
| 31 | 61 |
| 32 | 100 |
| 33 | 81/99 |

(/ indicates results of duplicate tests).

EXAMPLE 39

Spiro-oxazolidindiones prepared as described in the above examples were tested for their ability to reduce or inhibit sorbitol accumulation in the sciatic nerve of streptozotocinized (i.e., diabetic) rats by the procedure essentially described in U.S. Pat. No. 3,821,383. In the present study, the amount of sorbitol accumulation in the sciatic nerves was measured 27 hours after induction of diabetes. The compounds were administered orally at the dose levels indicated at 4, 8 and 24 hours following the administration of steptozotocin. The results obtained in this manner are presented below in terms of percent inhibition afforded by the test compound as compared to the case where no compound was administered (i.e., the untreated animal where sorbitol levels normally rise from approximately 50–100 mM/g. tissue to as high as 400 mM/g. tissue in the 27-hour test period). In this test values below 20 are not always experimentally and statistically significant.

| | % Inhibition at mg/kg Dosage | | |
|---|---|---|---|
| Compound of | 1.5 | 5 | 15 |
| 3 | 28 | — | — |
| 28 | 8 | — | — |
| 29 | 35 | — | — |
| 32 | 44 | — | — |
| 33 | 33 | — | — |
| 34 | 14 | — | — |
| 35 | 41 | 67 | 88 |

What is claimed is:
1. A compound of the formula

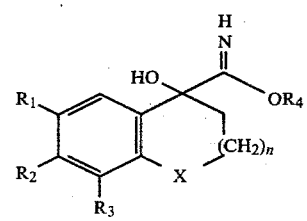

wherein
X is selected from the group consisting of oxygen and sulfur;
n is one or two;
$R_1$, $R_2$ and $R_3$ are each selected from the group consisting of hydrogen, chloro, bromo, fluoro, alkyl of 1 to 3 carbon atoms, phenyl and monosubstituted phenyl, wherein said substituent is selected from the group consisting of chloro, bromo, fluoro, hydroxyl, alkyl of 1 to 3 carbon atoms and alkoxy of 1 to 3 carbon atoms;

and $R_4$ is selected from the group consisting of alkyl of 1 to 4 carbon atoms, benzyl and monosubstituted benzyl, wherein said substituent is selected from the group consisting of chloro, bromo, fluoro, hydroxy, alkyl of 1 to 3 carbon atoms and alkoxy of 1 to 3 carbon atoms.

2. A compound of claim 1 wherein X is oxygen and n is one.

3. A compound of claim 2 wherein $R_1$ is chloro and $R_2$ and $R_3$ are each hydrogen.

4. A compound of claim 3 wherein $R_4$ is ethyl.

* * * * *